(12) United States Patent
Lesage et al.

(10) Patent No.: US 9,421,072 B2
(45) Date of Patent: Aug. 23, 2016

(54) VIBRATORY INSTRUMENT WITH AN INTERCHANGEABLE TOOL

(75) Inventors: Patrick Lesage, Saint Malo (FR); Jean-Michel Richer, Bruges (FR); Alain Pinel, Martignas sur Jalle (FR)

(73) Assignee: Societe Pour La Conception Des Applications Des Techniques Electroniques, Merignac (FR)

( * ) Notice: Subject to any disclaimer, the term of this patent is extended or adjusted under 35 U.S.C. 154(b) by 93 days.

(21) Appl. No.: 13/583,398

(22) PCT Filed: Mar. 3, 2011

(86) PCT No.: PCT/FR2011/050444
§ 371 (c)(1),
(2), (4) Date: Sep. 7, 2012

(87) PCT Pub. No.: WO2011/110774
PCT Pub. Date: Sep. 15, 2011

(65) Prior Publication Data
US 2013/0040263 A1 Feb. 14, 2013

(30) Foreign Application Priority Data
Mar. 12, 2010 (FR) ..................................... 10 51803

(51) Int. Cl.
*A61C 17/20* (2006.01)
*A61C 1/14* (2006.01)
(Continued)

(52) U.S. Cl.
CPC . *A61C 1/148* (2013.01); *A61C 3/03* (2013.01); *A61B 17/320068* (2013.01); *A61B 2017/00477* (2013.01); *A61C 1/10* (2013.01)

(58) Field of Classification Search
CPC .............. A61C 7/00; A61C 7/10; A61C 7/12; A61C 7/36; A61C 7/006; A61C 7/282; A61C 8/0096; A61C 17/20; A61C 17/0202; A61C 1/148; Y10S 37/904
USPC ......... 433/114, 117, 118, 119, 122, 123, 126, 433/127, 128, 129, 146, 147
See application file for complete search history.

(56) References Cited

U.S. PATENT DOCUMENTS 3,589,012 A * 6/1971 Richman .............. B23Q 1/0036
433/86
3,624,908 A * 12/1971 Ricketts et al. .......... A61C 3/06
433/118
(Continued)

FOREIGN PATENT DOCUMENTS

AT   EP 2160997 A1 *  3/2010 ............. A61C 1/148
DE   WO 9908617 A1 *  2/1999 ......... A61B 17/1615
(Continued)

OTHER PUBLICATIONS

Translation of wo02069829 a1.*
(Continued)

*Primary Examiner* — Nicholas Lucchesi
*Assistant Examiner* — Matthew Saunders
(74) *Attorney, Agent, or Firm* — Workman Nydegger

(57) ABSTRACT

A vibratory instrument includes a tool releasably mounted on a tool carrier designed to be coupled with a vibration generator device. The tool includes in succession along a longitudinal axis: a working portion presenting a free end for reproducing the vibration transmitted by the vibration generator device; a coupling portion; and an elastically-deformable attachment portion disposed upstream from the coupling portion. The tool carrier includes in succession along a longitudinal axis: a housing receiving the attachment portion of the tool; and a coupling bearing surrounding the coupling portion of the tool, at least in part. The attachment portion of the tool presents outside dimensions that are adapted relative to the inside dimensions of the housing of the tool carrier to prevent contact between the attachment portion and the housing when the coupling portion of the tool is in contact with the coupling bearing of the tool carrier.

14 Claims, 10 Drawing Sheets

(51) Int. Cl.
*A61C 3/03* (2006.01)
*A61B 17/32* (2006.01)
*A61B 17/00* (2006.01)
*A61C 1/10* (2006.01)

(56) References Cited

U.S. PATENT DOCUMENTS

| | | | | |
|---|---|---|---|---|
| 4,014,099 A | * | 3/1977 | Bailey | A61C 1/141 433/128 |
| 4,235,253 A | * | 11/1980 | Moore | A61C 15/047 132/322 |
| 4,283,175 A | | 8/1981 | Nash | |
| 4,571,184 A | * | 2/1986 | Edwardson | A61C 3/06 433/166 |
| 4,811,445 A | * | 3/1989 | Lagieski | A46B 5/0095 15/104.94 |
| 4,834,653 A | * | 5/1989 | Edwardson | A61C 1/07 433/118 |
| 4,976,625 A | * | 12/1990 | Weissman | A61C 1/07 433/118 |
| 4,984,985 A | | 1/1991 | Edwardson | |
| 5,000,684 A | * | 3/1991 | Odrich | A61C 15/00 15/22.1 |
| 5,505,617 A | * | 4/1996 | Skeppmark | A61C 1/07 433/118 |
| 5,655,906 A | * | 8/1997 | Coss | A61C 17/20 433/115 |
| 5,873,844 A | * | 2/1999 | Campero | A61H 23/0218 433/119 |
| 6,186,789 B1 | * | 2/2001 | Hugo | A61C 3/02 433/119 |
| 6,312,256 B1 | | 11/2001 | Dieras et al. | |
| 6,553,604 B1 | * | 4/2003 | Braun | A46B 9/04 15/167.1 |
| 6,602,073 B2 | * | 8/2003 | Schilling | A61C 17/20 433/117 |
| 6,729,877 B2 | * | 5/2004 | Rahman | A61C 3/00 433/141 |
| 6,872,125 B2 | * | 3/2005 | Harrel | 451/28 |
| 6,993,804 B1 | * | 2/2006 | Braun | A46B 9/005 15/110 |
| 7,677,890 B2 | * | 3/2010 | Turner | A61C 1/05 433/127 |
| 7,941,886 B2 | * | 5/2011 | Chenvainu | A46B 9/005 15/22.1 |
| 8,167,616 B2 | * | 5/2012 | Jamnia | A61C 3/00 433/143 |
| 8,677,545 B2 | * | 3/2014 | Vitt | A46B 5/002 15/167.1 |
| RE45,141 E | * | 9/2014 | Fischer | 15/110 |
| 2001/0017448 A1 | * | 8/2001 | Suzuki | B23B 31/202 279/52 |
| 2002/0031744 A1 | * | 3/2002 | Mossle | A61C 17/20 433/119 |
| 2004/0128784 A1 | * | 7/2004 | Ben-Ari | A46B 7/06 15/167.1 |
| 2004/0177462 A1 | * | 9/2004 | Brown, Jr. | A46B 3/16 15/167.1 |
| 2008/0178401 A1 | * | 7/2008 | Claire-Zimmet | A46B 5/002 15/22.2 |
| 2011/0311944 A1 | * | 12/2011 | Earthman | A61B 9/00 433/119 |

FOREIGN PATENT DOCUMENTS

| | | | | |
|---|---|---|---|---|
| DE | 19947325 A1 | * | 4/2001 | A61B 17/16 |
| DE | 102005058879 A1 | * | 6/2007 | A61C 3/03 |
| DE | 102007024809 A1 | * | 11/2008 | A61C 1/144 |
| EP | 2022437 A1 | | 2/2009 | |
| JP | 2002065700 A | | 3/2002 | |

OTHER PUBLICATIONS

Translation of DE 102005058879 a1.*
International Search Report for PCT/FR2011/050444, Oct. 11, 2011.

* cited by examiner

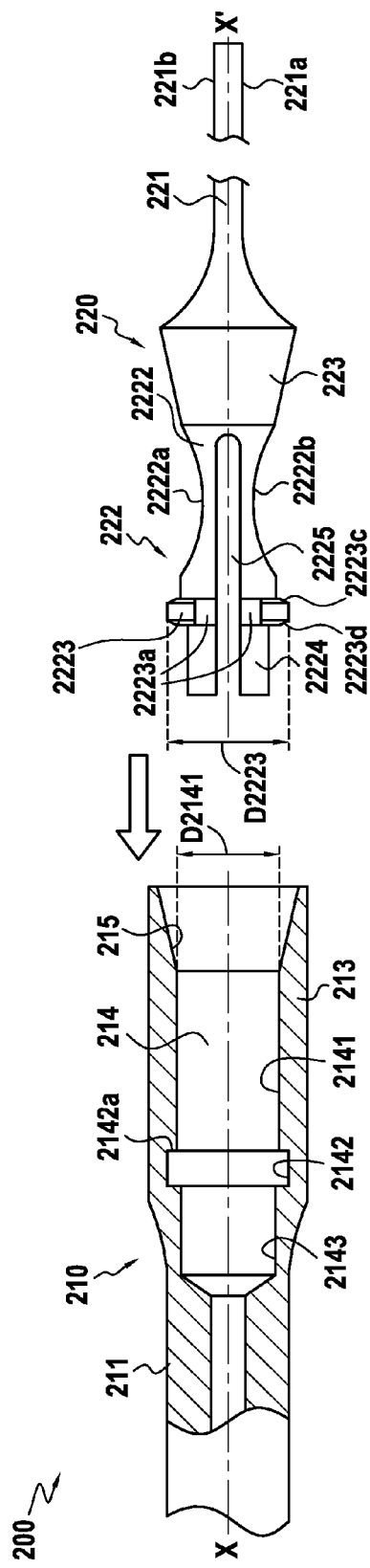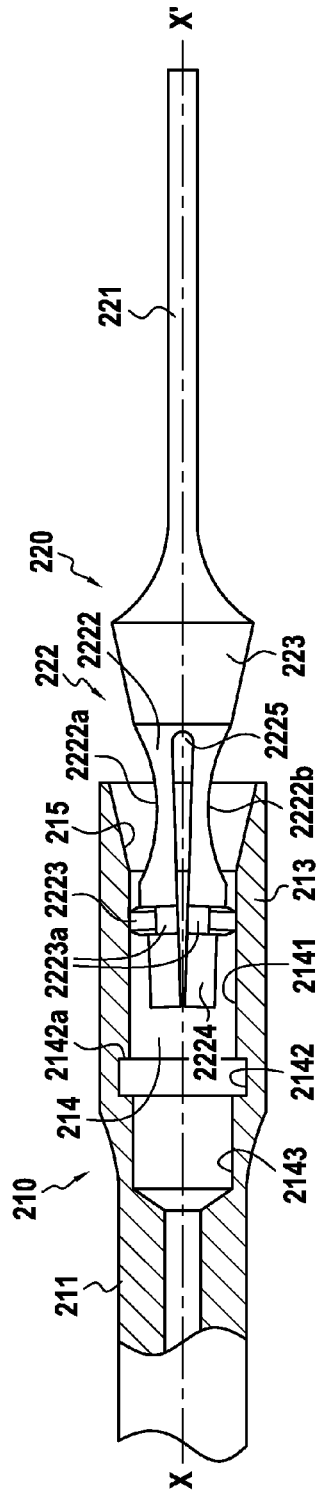
FIG.5A
FIG.5B

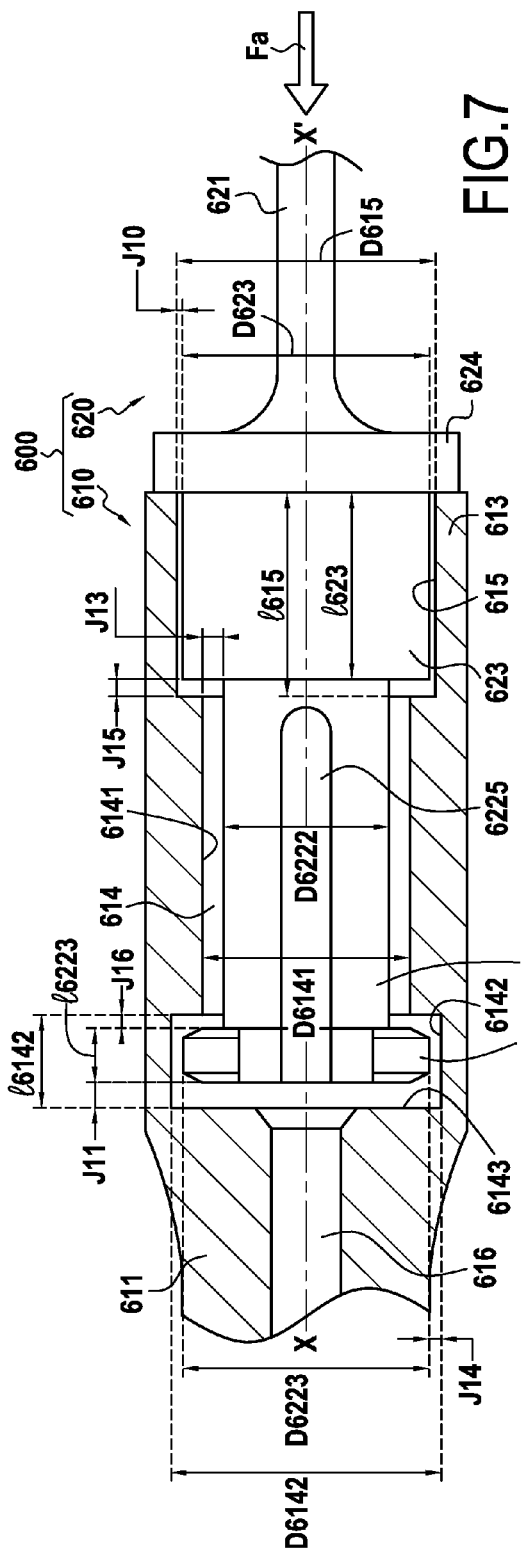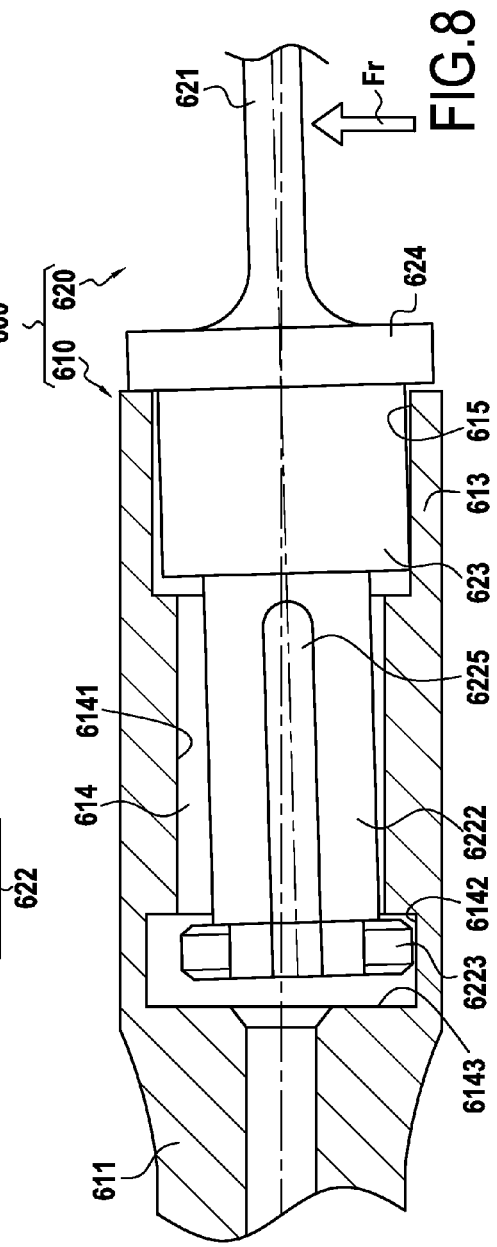
FIG.7
FIG.8 ary instrument needs to be properly screwed onto the handpiece and tightened sufficiently to obtain good mechanical coupling with the transducer, with it being possible for the transducer to use a dynamometer clamp for this purpose.
VIBRATORY INSTRUMENT WITH AN INTERCHANGEABLE TOOL

FIELD AND BACKGROUND OF THE INVENTION

The present invention relates to dental treatment appliances and more particularly to ultrasound appliances, such as appliances for removing scale, surfacing (eliminating biofilms), or cutting (cavities or preparing for a prosthesis), etc., which appliances include instruments that vibrate at ultrasound frequencies.

FIG. 1 shows an ultrasound treatment appliance 100 that comprises an ultrasound generator 110 connected to a handpiece 120 by a cord 111. A vibratory instrument 130, also referred to as a "sonotrode" or an "insert" or a "tip" that is designed to vibrate at sound or ultrasound frequencies is mounted on the top portion of the handpiece 120. In well-known manner, the handpiece 120 includes a transducer (not shown) e.g. constituted by a piezoelectric material and mechanically coupled to the insert 130 in such a manner as to transmit vibratory waves thereto at an amplitude that is determined as a function of the power delivered by the ultrasound generator 110.

As shown in FIG. 2, the vibratory instrument 130 is mainly constituted by two portions, a base or proximal portion 133 that is designed to be fastened rigidly on an element 123 that is secured to the transducer (not shown) of the handpiece 120, and a working portion or tool 132 that is designed to reproduce the vibration transmitted by the handpiece 120. The vibratory instrument 130 is generally fitted to the handpiece 120 by screw-fastening, with the base 133 of the instrument including tapping 133a that is screwed onto a fastener element 123 secured to the transducer and having a complementary thread 123a.

The working portion or tool 132 corresponds to the "useful" portion of the instrument, i.e. the portion with which the treatment is performed. The shape of the working portion of the instrument, and in particular the shape of its end 132a, is determined as a function of the treatment to be performed. By way of example, the instrument 130 presents a working portion 132 in which the shape of its end 132a is adapted to scale-removal treatment. FIGS. 3A to 3C show examples of instruments in which the working portions or tools are of shapes that are adapted to perform the following treatments respectively: removing scale and/or foreign matter (insert 140, FIG. 3A); preparatory treatments prior to putting a prosthesis in place (insert 150, FIG. 3B); and non-traumatic extraction and disengagement treatments (insert 160, FIG. 3C). Other examples of vibratory instruments are described in particular in documents U.S. Pat. No. 6,312,256 and U.S. Pat. No. 4,283,175.

On each new treatment, and even at certain stages in a single treatment, the practitioner needs to change the instrument on the handpiece, i.e. to unscrew the base of the instrument that was previously being used and to screw on another instrument that is adapted to the new treatment or to the following step of the treatment. During a single working day, the practitioner may need to repeat this operation a large number of times. However, although this operation is not in itself difficult, the practitioner must nevertheless pay sufficient attention thereto on each occasion in order to ensure that the instrument is properly assembled. For good operation, the vibratory instrument needs to be properly screwed onto the handpiece and tightened sufficiently to obtain good mechanical coupling with the transducer, with it being possible for the transducer to use a dynamometer clamp for this purpose.

Consequently, there is a need to reduce the time taken and to simplify the manipulation when changing an instrument, and more particularly when changing a working portion or tool.

Document JP 2002/065700 discloses a brush removably mounted on a tool-carrier secured to an ultrasound handpiece. Nevertheless, in that document, the system for attaching the brush to the tool carrier is adapted to allow good transmission of vibration to a brush, i.e. to a tool that is not rigid and of mass that is considerable. In addition, in the system described in that document, the coupling and attachment portions are the same. Such an attachment system is unsuitable for properly transmitting ultrasound vibration to tools or working portions that are rigid, such as those described above.

OBJECT AND SUMMARY OF THE INVENTION

An object of the present invention is to propose a solution that makes it possible to mount the working portion or tool of a vibratory instrument in releasable manner without it being necessary on each occasion to unscrew the entire instrument from the handpiece, while nevertheless ensuring good transmission of (sound or ultrasound) vibration from the handpiece to the working portion of the instrument.

This object is achieved by a vibratory instrument comprising a tool releasably mounted on a tool carrier, said tool carrier being designed to be mechanically coupled in rigid manner with a vibration generator device, the tool comprising in succession along a longitudinal axis: a working portion presenting a free end for reproducing the vibration transmitted by the vibration generator device; a coupling portion; and an elastically-deformable attachment portion disposed upstream from the coupling portion;

the tool carrier comprising in succession along a longitudinal axis: a housing receiving the attachment portion of said tool; and a coupling bearing surrounding the coupling portion of the tool, at least in part; and the attachment portion of the tool presenting outside dimensions that are adapted relative to the inside dimensions of the housing of the tool carrier so as to prevent contact between said attachment portion and said housing when the coupling portion of the tool is in contact with the coupling bearing of the tool carrier.

Thus, when an axial and/or radial thrust force is applied to the working portion of the tool, i.e. when the working portion is put into contact with the article that is to be treated, e.g. a tooth, the only contact between the tool carrier and the tool is situated between the coupling portion of the tool and the coupling bearing of the tool carrier. Consequently, good transmission of vibration from the tool carrier to the tool is ensured, by avoiding any damping that might occur between them as a result of contact between portions of the tool and the tool carrier other than the matching coupling elements.

Good transmission of vibration between the tool carrier and the tool is also ensured by the fact that the coupling portion of the tool is placed between its attachment portion and its working portion. Thus, the vibration received from the coupling bearing of the tool carrier by the coupling portion of the tool is transmitted directly to the working portion without needing to pass via other portions of the tool that might diminish the amplitude of the ultrasound waves.

In addition, by means of its elastically-deformable attachment portion, the tool of the present invention can be assembled in the tool carrier quickly and easily. Similarly, the tool of the present invention can be removed just as quickly and easily from the tool carrier. Consequently, since the working portion of the vibratory instrument in the present invention is incorporated in a tool that can be quickly and easily mounted on and dismounted from a tool carrier secured to the vibration generator device, the working portion may be changed in a short time, in particular in a time that is short compared with the time required for changing the working portion using prior art vibratory instruments that involve complete dismounting and mounting respectively of two different instruments on the vibration generator device.

In variant embodiments of the vibratory instrument of the invention, the coupling portion of the tool and the coupling bearing of the tool carrier may present complementary frustoconical shapes, or cylindrical shapes, or indeed both first portions of complementary frustoconical shape and second portions of cylindrical shape.

When the coupling portion of the tool and the coupling bearing of the tool carrier present cylindrical shapes, the coupling portion of the tool includes an axial abutment at its end joining the working portion of said tool, which axial abutment presents a diameter greater than the diameter of the coupling bearing of the tool carrier. When the coupling portion of the tool and the coupling bearing of the tool carrier present complementary frustoconical shapes, those two elements themselves form an axial abutment system.

According to an additional characteristic of the invention, said attachment portion of the tool includes a retaining element disposed upstream from the coupling portion, and the housing of the tool carrier includes a retaining portion receiving the retaining element of the tool.

According to another additional characteristic of the invention, the coupling portion of the tool includes a radial abutment, and the tool carrier includes an empty segment receiving said radial abutment, the radial abutment and the empty segment forming a rotation-limiter device for limiting turning of the tool in the tool carrier.

In an aspect of the invention, the resilience of the attachment portion is obtained by forming at least one longitudinal slot therein.

The attachment portion may also include at least one portion of reduced section substantially in the center of said attachment portion.

According to an additional characteristic of the invention, the tool carrier includes an internal channel suitable for co-operating with an internal channel in said handpiece, and the tool includes an internal channel suitable for co-operating with the internal channel of the tool carrier and opening out into the working portion.

The present invention also provides an ultrasound dental treatment appliance comprising at least one surgical handpiece connected to a vibration generator and characterized in that it further comprises at least one vibratory instrument according to the present invention.

BRIEF DESCRIPTION OF THE DRAWINGS

Other characteristics and advantages of the invention appear from the following description of particular embodiments of the invention, given as non-limiting examples, with reference to the accompanying drawings, in which:

FIGS. 5A to 5C show an operation of mounting the ultrasound tool in the tool carrier of the FIG. 4 vibratory instrument;

FIGS. 7 and 8 are section views of a vibratory instrument in accordance with another embodiment of the invention;

DETAILED DESCRIPTION OF EMBODIMENTS OF THE INVENTION

The present invention provides a novel design for an instrument or vibratory insert (also known as a "tip" or as a "sonotrode") that is made up of at least two separable elements, namely a first element corresponding to a vibratory tool having an end (working portion) that is to reproduce sound or ultrasound vibration, and a tool carrier for mechanically coupling in rigid manner with a device for generating sound or ultrasound vibration such as an ultrasound generating handpiece. The tool and the tool carrier are made of materials that are relatively rigid, such as metals, metal alloys (steel), or carbon material type composites.

Figure 4:
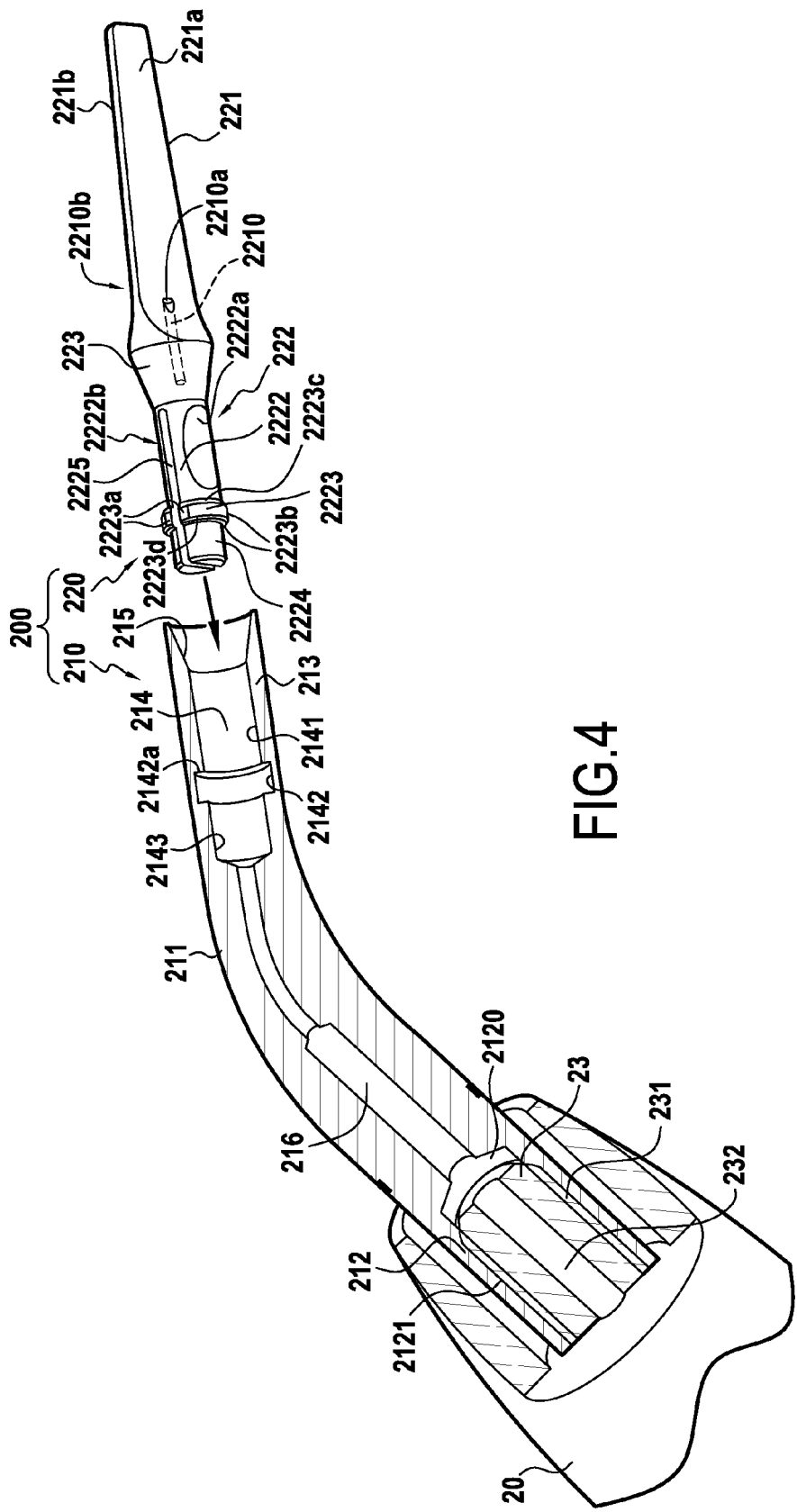
FIG. 4 is a perspective view, partially in section, prior to mounting a tool in a tool carrier of a vibratory instrument in accordance with an embodiment of the invention.

FIG. 4 shows a vibratory instrument or insert 200 in accordance with a first embodiment of the present invention and comprising a tool carrier 210 and a tool 220. The tool carrier 210 is a single-piece part that has a body 211 with a first end or base 212 for fastening rigidly to a handpiece 20. In well-known manner, the handpiece 20 is a generator of sound or ultrasound vibration and it may include a transducer (not shown), e.g. made of a piezoelectric material and mechanically coupled in rigid manner to the insert so as to transmit vibratory waves thereto. In the embodiment described herein, the tool carrier 210 is rigidly fastened to the handpiece by being screwed onto a fastener element 23 secured to the transducer of the handpiece. For this purpose, the base 212 of the tool carrier 210 includes a recess 2120 having tapping 2121 formed in the wall thereof and suitable for co-operating with a thread 231 present on the element 23. Naturally, the shape and the fastener means (here tapping) between the base of the tool carrier and the handpiece could be different. In general, the shape and the fastener means of the base of the tool carrier are defined as a function of the shape and the fastener means of the fastener element present on the handpiece. The tool carrier may also be permanently fastened to the handpiece, e.g. by welding, or it may correspond merely to an extension thereof. The tool carrier shown in FIG. 4 presents a curved shape to facilitate access to the site for treatment. Nevertheless, depending on the site in question, the tool carrier could present other types of shape, and in particular it could be even more curved, or on the contrary it could have a straight shape.

As shown in FIGS. 4 and 5A, the body 211 of the tool carrier 210 extends from the base 212 to a second end 213 and comprises in succession along a longitudinal axis XX' (FIG. 5A): a housing 214 for receiving an attachment portion 222 of the tool 220; and a coupling bearing 215 for surrounding at least in part and for co-operating with a coupling portion 223 of the tool 220, as explained in detail below. The housing 214 is formed by a cavity formed inside the tool carrier 210 at its end 213. The housing 214 presents a shape that varies, forming, starting from the coupling bearing 215 and going to the end of the housing 214: a portion 2141 of small section; a retaining portion 2142; and an end 2143. The coupling bearing 215, which in this example presents a female frustoconical shape on its inside surface, is designed to provide mechanical coupling with the tool 220, as explained below. The retaining portion 2142 forms a groove that presents a rim 2142a that enables the tool 220 to be retained once it has been inserted in the housing 214. The end 2143 is for receiving the end of the attachment portion of the tool 220. The end 2143 is connected to the end of the recess 2120 of the base 212 via an internal flow channel 216 formed inside the body 211 and designed to co-operate with an internal channel 232 of the fastener element 23 of the handpiece.

The ultrasound tool 220 mainly comprises three portions arranged in succession along the longitudinal axis XX', namely: a first portion referred to as its "working" portion 221; a second portion corresponding to a coupling portion 223; and a third portion referred to as its "attachment" portion 222. The working portion corresponds to the "useful" portion of the insert, i.e. the portion with which the treatment is performed. The shape of the working portion of the insert, and in particular the shape of its end is determined as a function of the treatment that is to be performed. In the embodiment described herein, the working portion 221 presents a flat shape defining two faces 221a and 221b. This shape is suitable in particular for removing foreign matter, i.e. "debridement". The working portion may also be structured and/or include a surface coating (e.g. an abrasive coating). As shown in FIG. 4, the tool 220 also includes an internal channel 2210 that opens out into both faces 221a and 221b via openings 2210a and 2210b. The channel 2210 serves to receive a fluid that is delivered from the handpiece via the internal channel 232 and conveyed as far as the tool by the internal channel 216 of the tool carrier.

The attachment portion 222 corresponds to the portion that is inserted in the housing 214 of the tool carrier 210. The attachment portion 222 includes an elongate portion 2222, a retaining element 2223, and a guide portion 2224. The attachment portion 222 also includes a slot 2225 that extends longitudinally in the guide portion 2224, the retaining element 2223, and the elongate portion 2222. The longitudinal slot 2225 has the function of imparting a capacity for elastic deformation to the attachment portion 222 of the tool 220 so as to enable the tool 220 to be inserted in and removed from the housing 214 in the tool carrier 210. Preferably, the slot 2225 extends solely in the attachment portion 222 and not in the coupling portion 223. If the slot 2225 were to extend also in the coupling portion 223, it would reduce the rigidity of the coupling portion, and that could have the effect of damping the vibration passing via said portion to the working portion of the tool. In addition, still with the slot extending into the coupling portion, the coupling portion would be capable of deforming, thereby reducing its (coupling) contact area with the coupling bearing of the tool carrier.

Figure 5C:
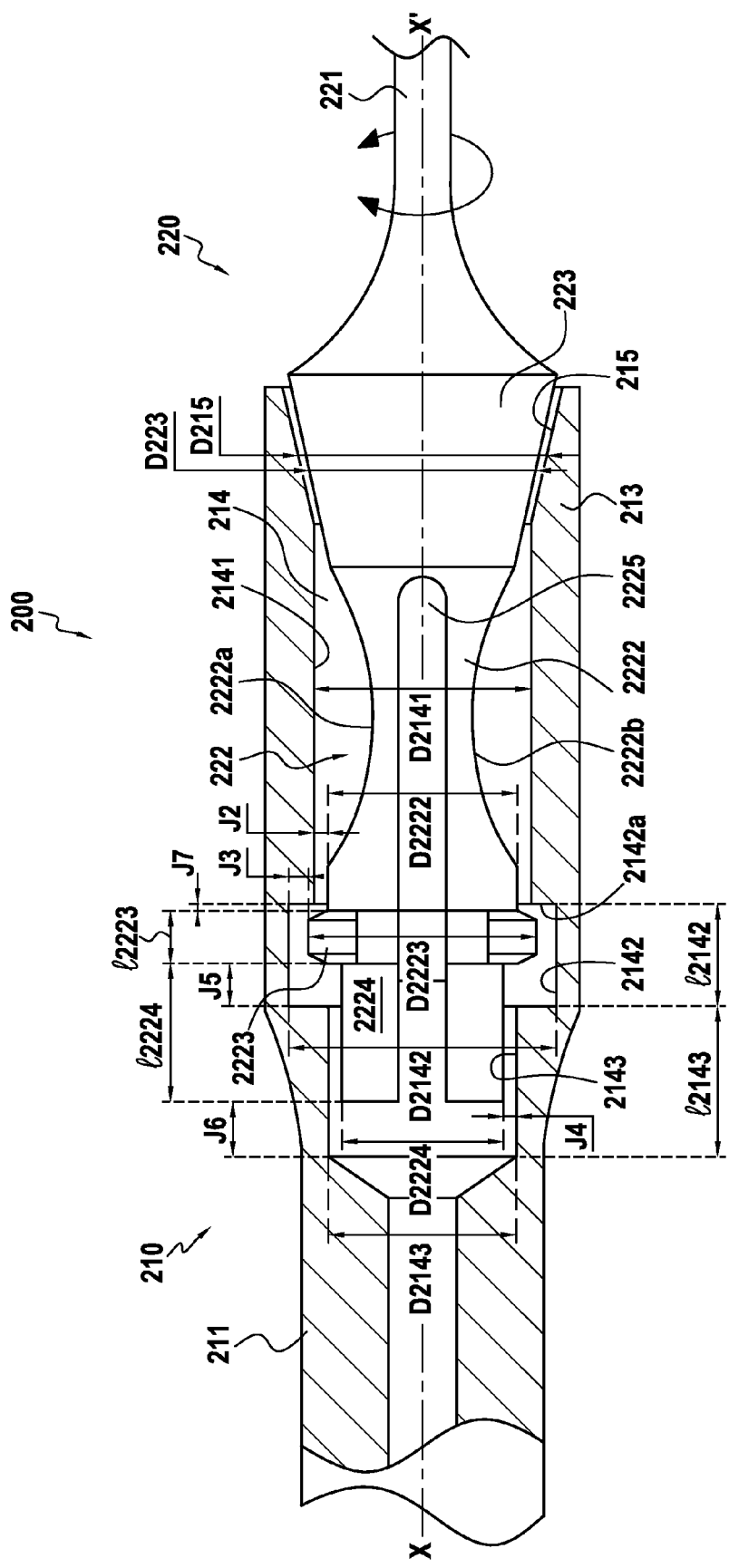
Figure 6:
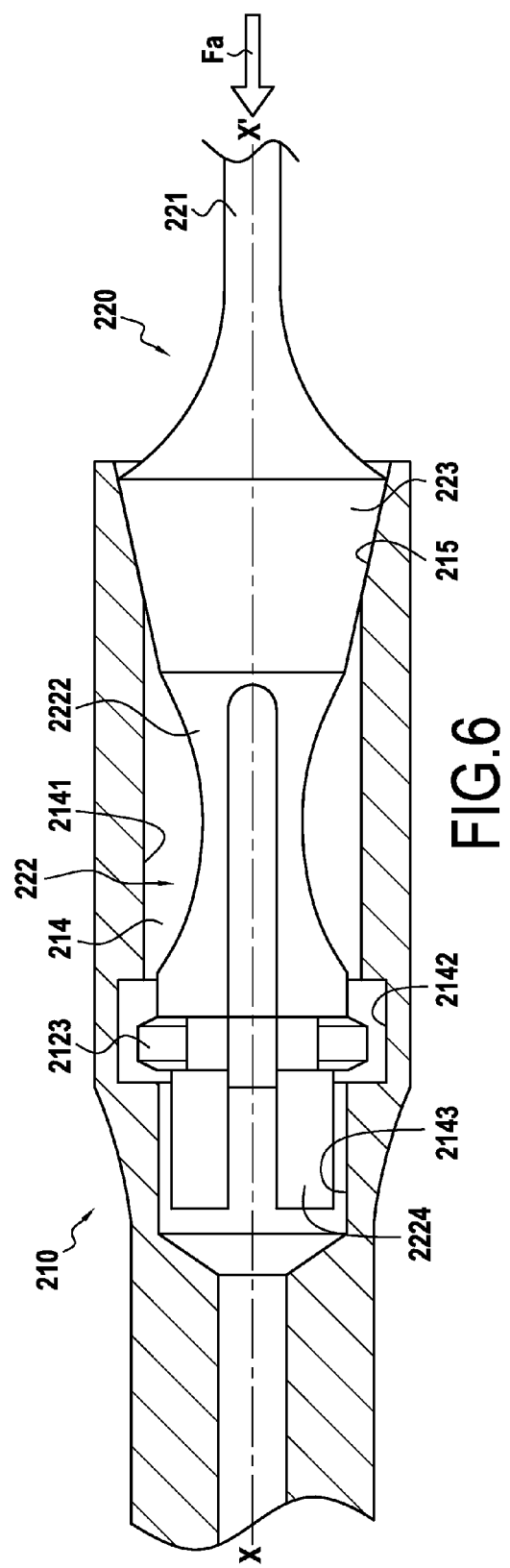
FIG. 6 shows the FIG. 5C vibratory instrument when an axial thrust force is applied to the working portion of the tool.

FIGS. 5A to 5C show the tool 220 being inserted into the tool carrier 210. The attachment portion 222 of the tool 220 is inserted in the housing 214 of the tool carrier 210 by engaging the guide portion 2224 into the inlet of the housing (FIG. 5A). The retaining element 2223 that forms a ring projecting from the attachment portion 222 then comes into contact with the inside wall of the housing which forms a passage in the portion 2141 of reduced section, said passage having a diameter $D_{2141}$ less than the width $D_{2223}$ of the retaining element 2223 while the attachment portion is at rest. It is possible for the retaining element to pass through the portion 2141 of reduced section because of the presence of the longitudinal slot 2225 which enables the attachment portion 222 to deform elastically, and also because of the presence of flats 2223a and 2223b formed on the retaining element, each on either side of the slot 2225 (FIG. 5B). Each flat 2223a and 2223b extends in a direction that is perpendicular to the plane of the slot 2225. The distance between the flats 2223a and 2223b is less than or equal to the diameter $D_{2141}$ of the portion of reduced section. When the retaining element reaches the retaining portion 2142, the attachment portion 222 returns to its initial shape (FIGS. 5C and 6). The retaining element 2223 is then received in the space formed by the retaining portion 2142. The rim 2142a prevents the tool 220 from moving back out from the housing 214 of the tool carrier 210 so long as no significant traction force is applied to the tool.

In accordance with the present invention, in order to ensure that ultrasound waves are well transmitted between the tool carrier 210 and the tool 220, the dimensions of these two elements are determined in such a manner that when the coupling portion of the tool and the coupling bearing of the tool carrier are in so-called "working" contact, i.e. when axial and/or radial pressure is applied to the working portion of the tool, there is no other contact between the remainder of the other portions of the tool and the tool carrier, i.e. between the attachment portion of the tool and the housing of the tool carrier. When this working contact is not engaged, the tool is merely retained in the tool carrier by the retaining element of the attachment portion.

More precisely, and as shown in FIG. 5C, the coupling portion 223 of the tool 220 has a male frustoconical shape presenting a mean diameter $D_{223}$, while the inside surface of the coupling bearing 215 of the tool carrier 210 has a female frustoconical shape presenting a mean diameter $D_{215}$. These complementary shapes enable these two elements to be mutually engaged and coupled together. In addition, the difference between the diameters $D_{223}$ and $D_{215}$, and the differences in taper between the coupling portion 223 and the coupling bearing 215, both of which constitute machining tolerances for the conical engagement, have an influence on the penetration depth of the coupling portion 223 into the coupling bearing 215. Consequently, these differences are determined in such a manner that when the coupling portion of the tool and the coupling bearing of the tool carrier are in working contact, no other portions of these two elements are in contact. In FIG. 5C, the coupling portion 223 and the inside surface of the coupling bearing 215 present frustoconical shapes presenting substantially the same taper.

The retaining element 2223 of the attachment portion 222 of the tool presents a width $l_{2223}$ that is less than the width $l_{2142}$ of the retaining portion 2142 of the housing 214 of the tool carrier so as to leave medium-sized axial gaps or clearances $J_5$ and $J_7$ between these two portions.

The guide portion 2224 of the attachment portion 222 of the tool presents a length $l_{2224}$ that is shorter than the length $l_{2143}$ of the end 2143 of the housing 214 of the tool so as to leave a medium-sized axial gap or clearance $J_6$ between these two portions.

In its largest portion, the elongate portion 2222 of the tool presents a diameter $D_{2222}$ that is less than the diameter $D_{2141}$ of the portion 2141 of reduced section of the housing 214 of the tool carrier, so as to leave a minimum-sized radial gap or clearance $J_2$ between these two portions.

The retaining element 2223 of the tool presents a diameter $D_{2223}$ that is less than the diameter $D_{2142}$ of the retaining portion 2142 of the housing 214 so as to leave a medium-sized radial gap or clearance $J_3$ between these two portions.

The guide portion 2224 of the tool presents a diameter $D_{2224}$ that is less than the diameter $D_{2143}$ of the end 2143 of the housing so as to leave a medium-sized radial gap or clearance $J_4$ between these two portions.

The retaining element 2223 is placed on the attachment portion 222 of the tool at a determined location that enables a gap or clearance $J_7$ to be provided between the upstream face of the retaining element and the upstream edge of the retaining portion 2142 of the housing 214.

In accordance with the invention, the clearances $J_2$ to $J_7$ that are present between the portions of the attachment portion 222 of the tool and the portions of the housing 214 of the tool carrier are determined in such a manner as to prevent contact between the attachment portion 222 and the housing 214 when the coupling portion 223 and the inside surface of the coupling bearing 215 are in contact.

As shown in FIG. 6, when an axial thrust force Fa is exerted on the working portion 221 of the tool 220, only the coupling portion 223 of the tool and the coupling bearing 215 of the tool carrier 210 are in working contact, the other portions of the attachment portion of the tool and the housing of the tool carrier not being in contact. Thus, the ultrasound vibration received by the tool carrier from the handpiece is transmitted to the tool solely via the contact surface formed between the coupling portion 223 and the coupling bearing 215. In this way, there is no risk of this vibration being damped by contact between other portions of the tool and of the tool carrier, thus making it possible to obtain good transmission of ultrasound vibration between the tool carrier and the tool. Likewise, when a lateral or radial thrust force is applied to the working portion 221, the same configuration is obtained, i.e. contact only between the coupling portion 223 of the tool and the coupling bearing 215 of the tool carrier 210, and no contact between the attachment portion of the tool and the housing of the tool carrier.

The clearance $J_7$ between the upstream face of the retaining element and the upstream edge of the retaining portion 2142 of the housing 214 is less than the length over which the coupling portion 223 extends so as to avoid the coupling portion from escaping completely from the tool carrier in certain positions of the instrument, i.e. so as to avoid it no longer being in a position facing at least a portion of the coupling bearing of the tool carrier.

As explained above, the tool needs to be made of a material that is sufficiently rigid to reproduce correctly the ultrasound vibration generated by the handpiece. Consequently, the presence of the longitudinal slot enables a capacity for deformation and resilience to be imparted to the attachment portion of the tool that are sufficient to enable the tool respectively to be inserted in and held in the tool carrier. The two portions of the attachment portion that are separated by the slot can be moved towards each other in order to allow the retaining element to pass through the portion of reduced section (FIG. 5B) and can subsequently return to their initial position once the retaining element has reached the retaining portion of the housing, thus making it possible to ensure that the tool is held in the tool carrier (FIG. 5C).

The tool is extracted from the tool carrier by exerting a traction force on the tool directed to leaving the housing, e.g. by pulling on the working portion in the direction opposite to the insertion direction. Under such circumstances, the attachment portion 222 of the tool 220 deforms to allow the retaining element 2223 to disengage from the retaining portion 2142 and pass through the portion 2141 of reduced section, as shown in FIG. 5B In order to further increase the capacity of attachment portion 222 of the tool 220 for elastic deformation, the portion 2222a and 2222b of reduced section (e.g. obtained by milling) are made in its elongate portion 2222, thus making it possible to reduce the thickness of the rigid material, locally. In addition, two flats 2223a are machined on the retaining element 2223 in order to enable it to pass into the housing of the tool carrier, and in particular into the portion 2141 of reduced section. The flats 2223a are made on either side of the slot 2225 and they extend in a direction perpendicular to the plane of the slot.

Furthermore, the retaining element 2223 may include chamfers 2223c and 2223d on its edges in order to facilitate insertion and removal of the tool into and out from the housing in the tool carrier. The chamfer 2223c serves in particular to facilitate disengaging the retaining element 2223 from the rim 2142a of the retaining portion 2142 when traction is exerted on the tool.

The width of the longitudinal slot 2225 is determined as a function of the deformation (here pinching deformation) of the attachment portion that is needed to allow the retaining element 2223 to pass into the portion 2141 of reduced section.

As shown in FIG. 6, the mechanical coupling between the tool carrier 210 and the tool 220 for transmitting ultrasound vibratory waves is achieved by putting the coupling bearing 215 of the tool carrier 210 into contact with the coupling portion 223 of the tool 220. In the embodiment described, these two portions present conical shapes that are complementary.

FIG. 7 shows another embodiment of a vibratory instrument of the invention. The FIG. 7 vibratory instrument differs from that shown in FIGS. 4 and 5A to 5C mainly in that the coupling portion of the tool and the coupling bearing of the tool both present a shape that is cylindrical instead of being frustoconical in shape, as above.

Like the vibratory instrument 200 described above, the vibratory instrument 600 of FIG. 7 is formed by a tool carrier 610 and a tool 620. The tool carrier 610 is a single-piece part that includes a body 611 presenting, like the above-described tool carrier 210, a first end or base (not shown in FIG. 7) for fastening rigidly to a handpiece. The shape of the base of the tool carrier and its means for fastening to the handpiece may be varied (tapping, permanent fastening, extension of the handpiece, etc.).

The second end 613 of the body 611 of the tool carrier 610 comprise in succession along a longitudinal axis XX': a coupling bearing 615 for surrounding a coupling portion 623 of the tool 620; and for co-operating therewith and with a housing 614 that is to receive an attachment portion 622 of the tool 620. The housing 614 presents a varying shape that going from the coupling bearing 615 to the end of the housing 614 forms: a portion 6141 of reduced section; a retaining portion 6142; and an end 6143. The end 6143 is connected to the end of the fastener base of the tool carrier (not shown in FIG. 7) via an internal flow channel 616 formed inside the body 611 for the purpose of co-operating with an internal channel in the fastener element of the handpiece.

The ultrasound tool 620 comprises in succession along the longitudinal axis XX': a working portion 621; a coupling portion 623; and an attachment portion 622; the coupling portion 623 further including an axial abutment 624 at its junction with the working portion 621. The tool 620 may also further include, like the above-described tool 220, an internal channel for receiving a fluid delivered from the handpiece via the internal channel of the tool carrier and opening out into the faces of the working portion via openings (not shown in FIG. 7).

The attachment portion 622 comprises an elongate portion 6222 and a retaining element 6223. The attachment portion 622 also includes a slot 6225 that extends longitudinally in the retaining element 6223 and the elongate portion 6222.

The tool 620 is inserted into and/or extracted from the tool carrier 610 by exerting a thrust and/or traction force on the tool, with the elastic deformation of the attachment portion 622 of the tool resulting from the presence of the slot 6225 and of the flats 6223a and 6223b that enable the retaining element 6223 of the tool to be engaged in and/or disengaged from the retaining portion 6142 of the tool carrier.

In addition, in accordance with the invention, the dimensions of these two elements are determined in such a manner that when the tool is mounted in the tool carrier, as shown in FIG. 7, the clearance present between the coupling portion of the tool and the coupling bearing of the tool carrier is less than the clearance present between the remainder of the portions of the tool and the tool carrier.

More precisely, the coupling portion 623 of the tool 620 presents a diameter $D_{623}$ that is less than the diameter $D_{615}$ of the coupling bearing 615 of the tool carrier 610 so as to leave medium-sized clearance $J_{10}$ between these two portions, thereby enabling them to be engaged one in the other.

The retaining element 6223 of the attachment portion 622 of the tool presents a width $l_{6223}$ that is less than the width $l_{6142}$ of the retaining portion 6142 of the housing 614 of the tool carrier so as to leave medium-sized axial clearances $J_{11}$ and $J_{16}$ between these two portions.

The elongate portion 6222 of the tool presents a diameter $D_{6222}$ that is less than the diameter $D_{6141}$ of the portion 6141 of reduced section of the housing 614 of the tool carrier so as to leave medium-sized radial clearance $J_{13}$ between these two portions.

The retaining element 6223 of the tool presents a diameter $D_{6223}$ that is less than the diameter $D_{6142}$ of the retaining portion 6142 of the housing 614 so as to leave medium-sized radial clearance $J_{14}$ between these two portions.

The coupling portion 623 of the tool 620 presents a length $l_{623}$ that is less than the length $l_{615}$ of the coupling bearing $l_{615}$ of the tool carrier 610 so as to provide medium-sized clearance $J_{15}$ between these two portions.

The retaining element 6223 is placed on the attachment portion 622 of the tool at a determined location that allows clearance $J_{16}$ to be provided between the upstream face of the retaining element and the upstream edge of the retaining portion 6142 of the housing 614.

In accordance with the invention, the clearances $J_{10}$, $J_{11}$ and $J_{13}$ to $J_{16}$ that are present between the portions of the attachment portion 622 of the tool and the portions of the housing 614 of the tool carrier are determined in such a manner as to prevent contact between the attachment portion 622 and the housing 614 when the coupling portion 623 and the inside surface of the coupling bearing 615 are in working contact.

As shown in FIG. 8, when a radial thrust force Fr is exerted on the working portion 621 of the tool 620, only the coupling portion 623 of the tool and the coupling bearing 615 of the tool carrier 610 are in working contact (points of contact between the two elements), the other portions of the attachment portion of the tool and of the housing of the tool carrier not being in contact, in particular because of the presence of the clearances $J_{13}$, $J_{14}$, and $J_{16}$. Thus, the ultrasound vibration received by the tool carrier from the handpiece is transmitted by the tool by contact between the coupling portion 623 and the coupling bearing 615. In this way, there is no risk of this vibration being damped by contact between other portions of the tool and of the tool carrier, thus making it possible to obtain good transmission of ultrasound vibration between the tool carrier and the tool.

When an axial thrust force Fa is applied to the working portion 621 of the tool 620 (FIG. 7), the mechanical coupling between the tool 620 and the tool carrier 610 takes place essentially via the axial abutment 624 of the tool that comes to bear against the end of the coupling bearing 615 of the tool carrier, the other portions of the attachment portion of the tool and of the housing of the tool carrier not being in contact, in particular because of the presence of the clearances $J_{11}$ and $J_{15}$.

The clearance $J_{16}$ between the upstream face of the retaining element and the upstream edge of the retaining portion 6142 of the housing 614 is less than the length over which the coupling portion 623 extends in order to prevent the coupling portion from escaping completely from the tool carrier in certain positions of the instrument and in order to prevent it no longer facing at least a portion of the coupling bearing of the tool carrier.

Figure 9:
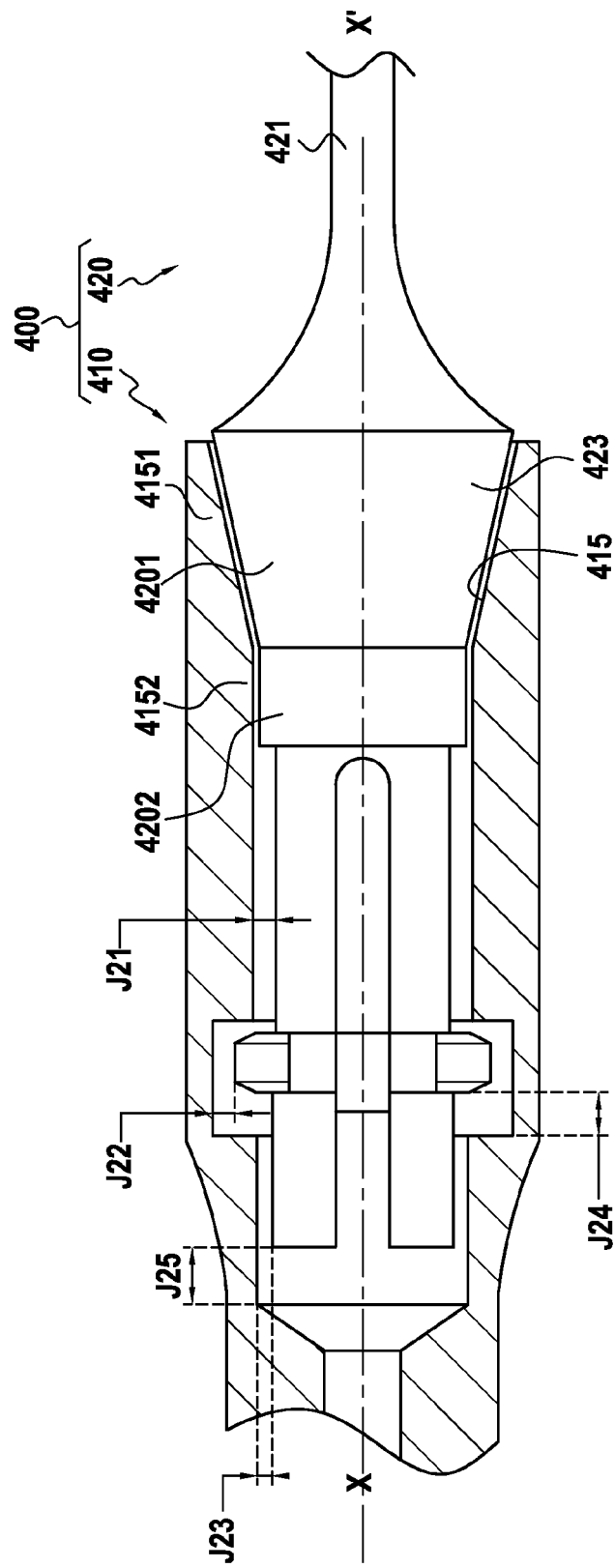
FIG. 9 is a section view of a vibratory instrument in accordance with yet another embodiment of the invention.

FIG. 9 shows another embodiment of a vibratory instrument of the invention. The vibratory instrument 400 of FIG. 9 differs from that shown in FIGS. 4 and 5A to 5C in that the coupling portion 423 of the tool 420 and the coupling bearing 415 of the tool 410 both present complementary cylindrical-and-conical shapes. More precisely, the coupling portion of the tool 420 comprises a frustoconical first portion 4201 and a cylindrical second portion 4202, while the coupling bearing 415 of the tool carrier 410 likewise includes a frustoconical first portion 4151 and a cylindrical second portion 4152.

The other elements or portions of the tool 420, i.e. the working portion and the attachment portion, and of the tool carrier 410, i.e. the housing, are identical to those of the above-described vibratory instrument 200.

In accordance with the invention, and as explained above, clearances $J_{22}$ to $J_{25}$ present between the attachment portion of the tool and the housing of the tool carrier, and also the differences in diameter and in taper between the frustoconical first portion 4201 of the tool 420 and the frustoconical first portion 4151 of the tool carrier 410 are defined in such a manner that when an axial and/or radial thrust force is applied to the working portion 421 of the tool 420, only the coupling portion 423 of the tool and the coupling bearing 415 of the tool carrier are in working contact, the other portions of the attachment portion of the tool and of the housing of the tool carrier not being in contact.

In the light of the embodiment described above, the person skilled in the art will have no difficulty in devising other embodiments of the vibratory instrument of the invention. In general, in order to optimize the transmission of vibration between the tool carrier and the tool, the dimensions of those two elements are determined so that firstly the axial clearance(s) between the attachment portion of the tool and the housing of the tool carrier is/are greater than the depth to which the coupling portion of the tool penetrates into the coupling bearing of the tool carrier, and secondly the radial clearance(s) between the attachment portion of the tool and the housing of the tool carrier is/are greater than the radial clearance present between the coupling portion of the tool and the coupling bearing of the tool carrier.

In the vibratory instruments 200, 400, and 600 described above, the tools 220 and 620 are mounted so as to be free to turn in the tool carriers 210 and 610, given the shapes of the surfaces of the contact bearings 2140 and 6140 of said tool carriers and of the coupling portions 2221 and 6221 of said tools. Under such circumstances, the tool automatically takes up an orientation (i.e. it turns) as a function of the surface with which it is in contact. By way of example, this freedom to move in rotation makes it possible to work over the entire periphery of a single tooth using the same tool.

Figure 10A:
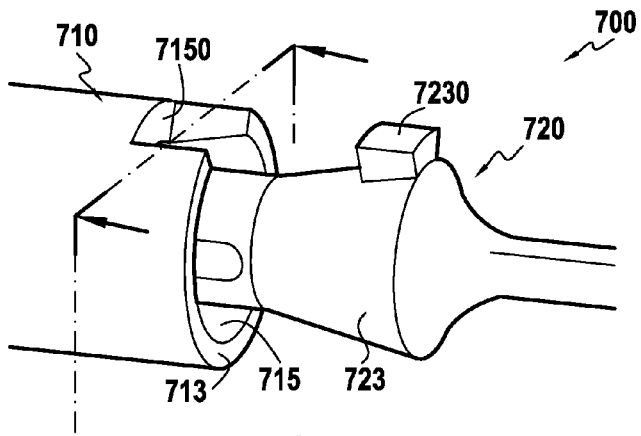
FIGS. 10A and 10B are respectively a perspective view and a section view showing a rotation-limiter device placed on the FIG. 4 vibratory instrument.
Figure 10B:
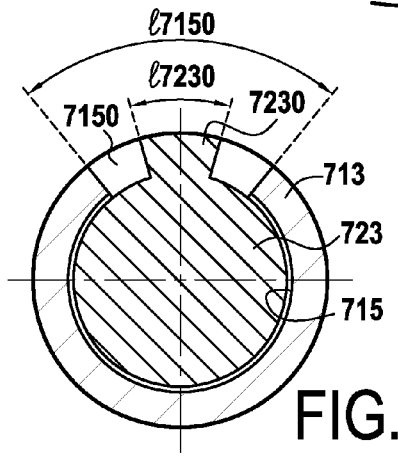

FIGS. 10A and 10B show an embodiment of a vibratory instrument 700 that differs from the instrument 200 shown in FIGS. 4 and 5A to 5C in that the coupling portion 723 of the tool 720 includes a radial abutment 7230 in the downstream portion of the coupling portion, and in that the coupling bearing 715 of the tool carrier 710 presents an empty segment 7150 in its free end 713. When the tool 720 is inserted into the tool carrier 710, the radial abutment 7230 is received in the empty segment to form a rotation-limiter device preventing the tool from turning in the tool carrier. The length of the arc $L_{7150}$ of the empty segment 7150 relative to the width $l_{7230}$ of the radial abutment 7230 define the angular limit on turning of the tool 720 in the tool carrier 710.

The other portions of the tool 720 and of the tool carrier 710 of the instrument 700 are identical to portions of the tool 220 and of the tool carrier 210 of the instrument 200 described above and they are not described again for simplicity.

Figure 11A:
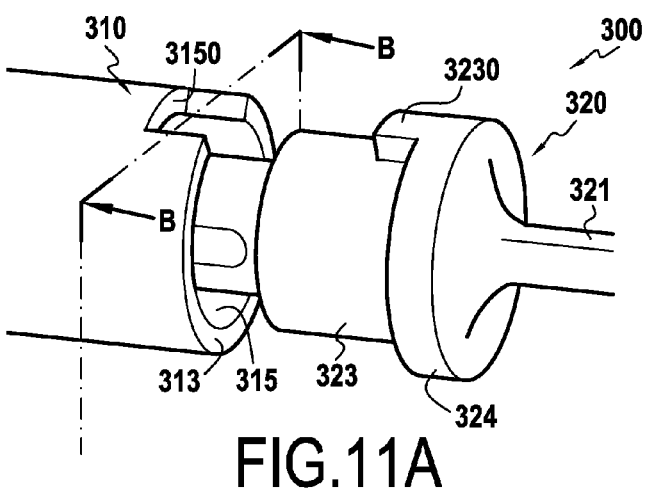
FIGS. 11A and 11B are respectively a perspective view and a section view showing a rotation-limiter device placed on the FIG. 7 vibratory instrument.
Figure 11B:
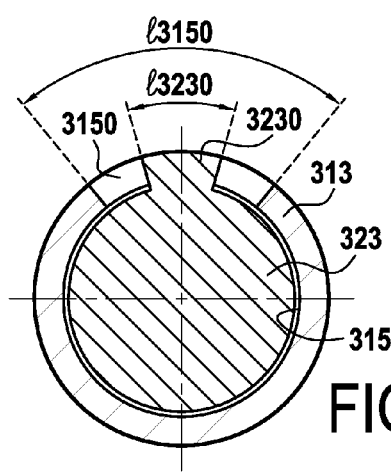

FIGS. 11A and 11B show an embodiment of a vibratory instrument 300 that differs from the instrument 600 described with reference to FIG. 8 in that the axial abutment 324 of the coupling portion 323 of the tool 320 includes a radial abutment 3230, and in that the coupling bearing 315 of the tool carrier 310 presents an empty segment 3150 at its free end 313. When the tool 320 is inserted in the tool carrier 310, the radial abutment 3230 is received inside the empty segment so as to form a rotation-limiter device for limiting turning of the tool in the tool carrier. The length of the arc $L_{3150}$ of the empty segment 3150 relative to the width $l_{3230}$ of the radial abutment 3230 defines the angular limit on turning of the tool 320 in the tool carrier 310.

The other portions of the tool 320 and of the tool carrier 310 of the instrument 300 are identical to those of the tool 620 and of the tool carrier 610 of the instrument 600 described above and they are not described again for simplicity.

In the embodiments shown in FIGS. 10A, 10B, 11A, and 11B, turning of the tool in the tool carrier may be blocked by having the width of the radial abutment of the tool match the length of the arc of the empty segment of the tool carrier.

It should also be observed that a tool that does not include a radial abutment element may also be used in a tool carrier that does include an empty segment, as described above.

In the light of the above description, the person skilled in the art will have no difficulty in devising other embodiments of the rotation-limiter device between the tool and the tool carrier.

Figure 1:
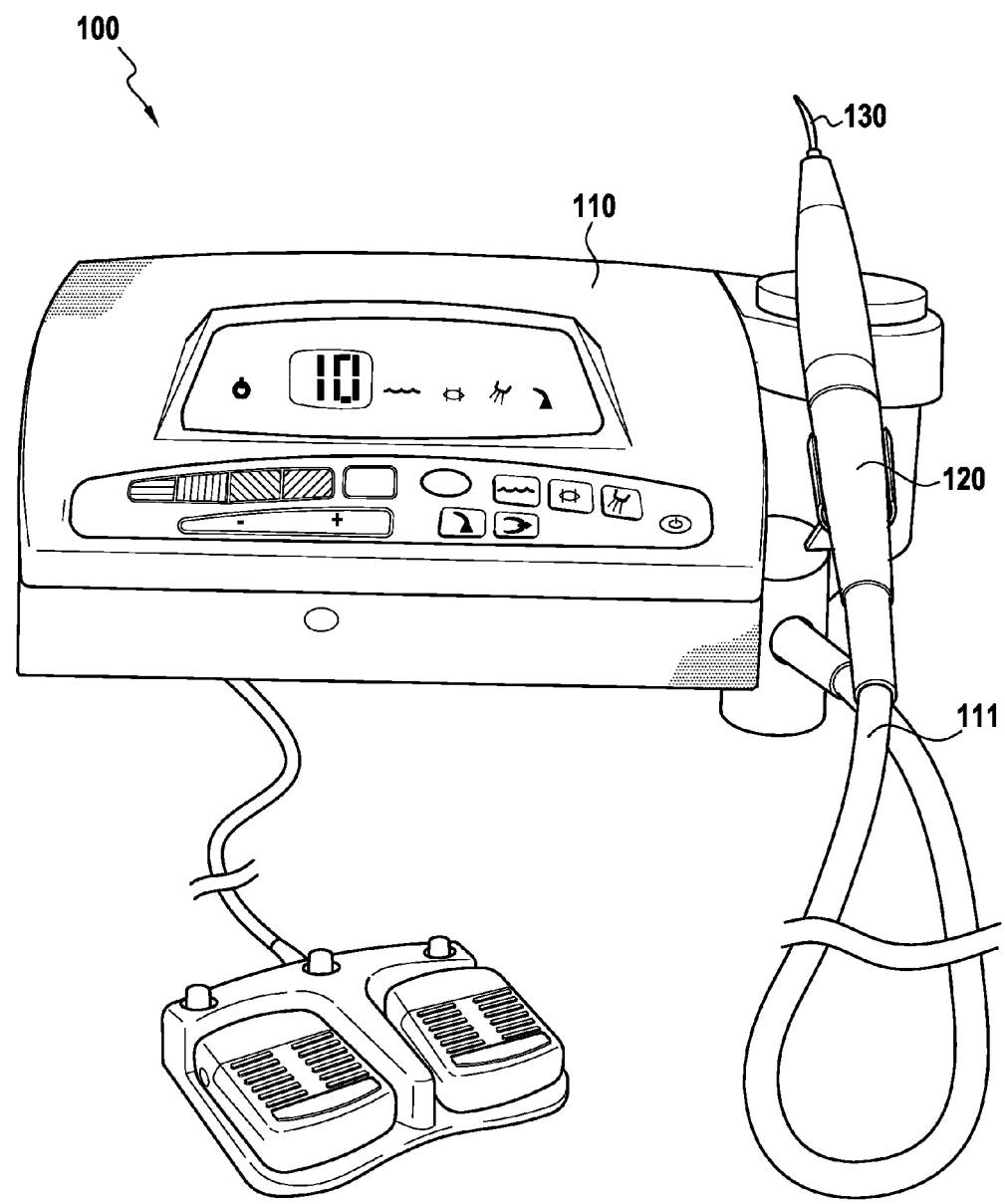
FIG. 1 is a perspective view of an ultrasound dental surgery appliance.
Figure 2:
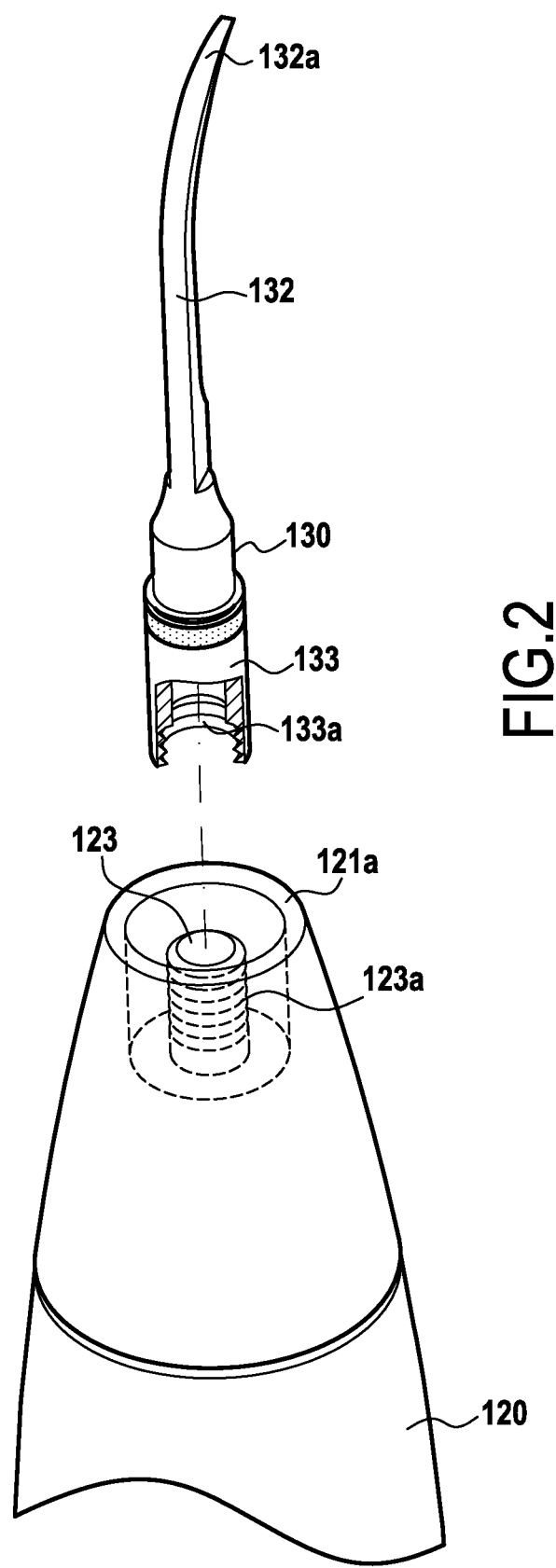
FIG. 2 is a perspective view of a vibratory instrument prior to being mounted on a handpiece in the prior art.
Figures 3A, 3B, 3C:
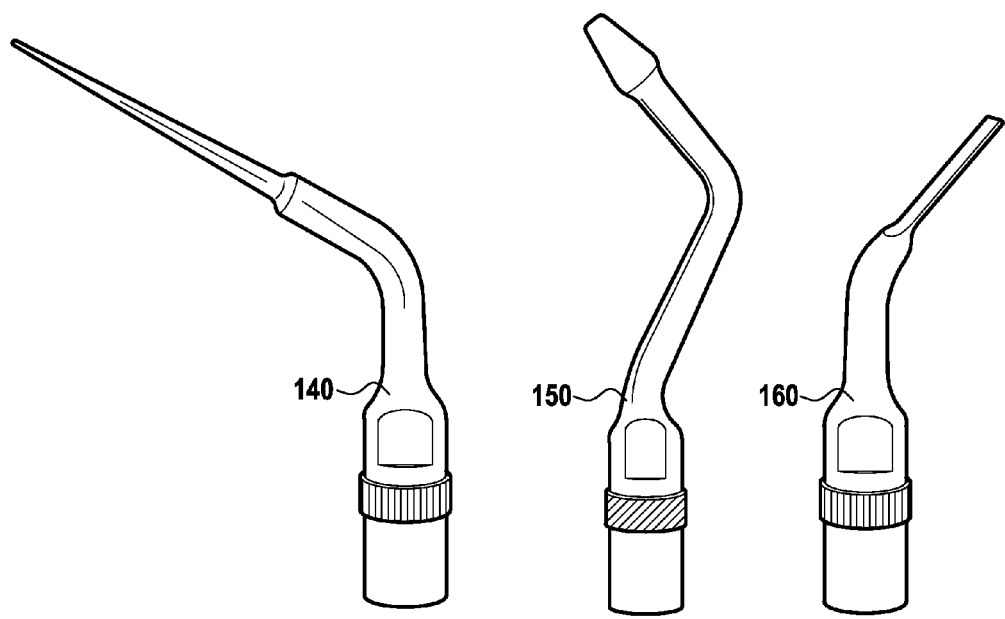
FIGS. 3A to 3C show examples of vibratory instruments that present different shapes.

Vibratory instruments or inserts of the invention may be used with peripheral appliances for dental use such as appliances for treatment using sound or ultrasound vibration that, given their functions and their ergonomics, constitute finished products of the kind shown in above-described FIG. 1. Such inserts may also be used with appliances that are presented in the form of modules for being integrated (original equipment manufacturer (OEM) technology) with other modules in dedicated products such as workstations for dentists' offices.

The invention claimed is:

1. A vibratory instrument comprising a tool releasably mounted on a tool carrier, said tool carrier being configured to be mechanically coupled in rigid manner with a vibration generator device, said tool comprising in succession along a longitudinal axis: a working portion presenting a free end reproducing the vibration transmitted by the vibration generator device; a coupling portion; and an elastically-deformable attachment portion extending in an upstream direction from the coupling portion, the attachment portion being directly adjacent to the coupling portion; said tool carrier comprising in succession along a longitudinal axis: a housing and a coupling bearing, the housing being a cavity having an inside dimensions configured to receive the attachment portion of said tool, the housing surrounding at least in part the attachment portion, an inner surface of the housing extending from a portion of the coupling bearing; and the coupling bearing surrounding the coupling portion of the tool, at least in part; and the attachment portion of the tool presenting outside dimensions that are adapted relative to the inside dimensions of the housing of the tool carrier so as to prevent contact between said attachment portion and said housing when the coupling portion of the tool is in contact with the coupling bearing of the tool carrier, wherein the coupling portion of the tool includes a portion having a frustoconical shape, and the coupling bearing of the tool carrier includes a portion having a frustoconical shape that is complementary to the shape of said coupling portion, said coupling portion and the coupling bearing also forming an axial abutment system, wherein the attachment portion includes a longitudinal slot, the longitudinal slot extending only in the attachment portion and not in the coupling portion, and wherein an inside diameter of a downstream portion of the frustoconical shape of the coupling bearing is greater than an inside diameter of an upstream portion of the frustoconical shape of the coupling bearing, the downstream portion of the frustoconical shape being closer to the working portion than the upstream portion of the frustoconical shape is to the working portion.

2. A vibratory instrument according to claim 1, wherein the coupling portion of the tool includes an axial abutment at its end joining the working portion of said tool, the axial abutment serving to co-operate with the free end of the coupling bearing of the tool carrier.

3. A vibratory instrument according to claim 1, wherein the coupling portion of the tool includes a first portion of frustoconical shape that is extended by a second portion of cylindrical shape, and wherein the coupling bearing of the tool carrier comprises a first portion of frustoconical shape complementary to the shape of said coupling portion, and a second portion of cylindrical shape.

4. A vibratory instrument according to claim 1, wherein said attachment portion of the tool includes a retaining element disposed upstream from the coupling portion, and wherein the housing of the tool carrier includes a retaining portion receiving the retaining element of the tool.

5. A vibratory instrument according to claim 1, wherein the tool includes a radial abutment, and the tool carrier includes an empty segment receiving said radial abutment, the radial abutment and the empty segment forming a rotation-limiter device limiting turning of the tool in the tool carrier.

6. A vibratory instrument according to claim 1, wherein the attachment portion includes a longitudinal slot.

7. A vibratory instrument according to claim 6, wherein said attachment portion of the tool includes a retaining element disposed upstream from the coupling portion, and
   wherein the retaining element comprises two flats, each flat disposed on either side of the longitudinal slot and extending in a direction perpendicular to a plane including a length of said slot.

8. A vibratory instrument according to claim 4, wherein the attachment portion includes at least one portion of reduced section situated substantially in the center of said attachment portion.

9. A vibratory instrument according to claim 1, wherein the tool is made of a rigid material including at least a metal, a metal alloy, or carbon.

10. A vibratory instrument according to claim 1, wherein the tool carrier includes an internal channel suitable for co-operating with an internal channel in said handpiece, and the tool includes an internal channel suitable for co-operating with the internal channel of the tool carrier and opening out into the working portion.

11. An ultrasound dental treatment appliance comprising at least one surgical handpiece connected to a vibration generator and comprising at least one vibratory instrument as recited in claim 1.

12. A vibratory instrument according to claim 1, wherein the housing of the tool carrier is disposed upstream from the coupling bearing of the tool carrier.

13. A vibratory instrument according to claim 1, wherein the attachment portion includes a retaining element that forms a ring projecting radially from the longitudinal axis of the attachment portion.

14. A vibratory instrument according to claim 1, wherein the attachment portion includes an elongation portion, the elongation portion including a first portion and a second portion, an outer diameter of the first portion being less than an outer diameter of the second portion.

* * * * *